(12) United States Patent
Hanagasaki (10) Patent No.: US 7,766,876 B2
(45) Date of Patent: Aug. 3, 2010

(54) GASTROSTOMY CATHETER INTRODUCING DEVICE

(76) Inventor: Kazuo Hanagasaki, 3-6-8, Ikenokami, Shiroi-Shi, Chiba-Ken (JP)

( * ) Notice: Subject to any disclaimer, the term of this patent is extended or adjusted under 35 U.S.C. 154(b) by 500 days.

(21) Appl. No.: 11/823,721

(22) Filed: Jun. 28, 2007

(65) Prior Publication Data

US 2008/0058721 A1 Mar. 6, 2008

(30) Foreign Application Priority Data

Aug. 29, 2006 (JP) ............................. 2006-232075

(51) Int. Cl.
*A61M 5/178* (2006.01)
(52) U.S. Cl. ................... 604/164.11; 604/910
(58) Field of Classification Search ................ 604/104, 604/163, 164.01, 164.05, 164.09, 164.1, 604/164.11, 910
See application file for complete search history.

(56) References Cited

U.S. PATENT DOCUMENTS

| | | | |
|---|---|---|---|
| 5,792,119 A | | 8/1998 | Marx |
| 5,935,107 A | * | 8/1999 | Taylor et al. ............ 604/164.04 |
| 7,186,238 B2 | * | 3/2007 | Elbert et al. ............ 604/164.01 |
| 2005/0273078 A1 | | 12/2005 | Whitmore, III et al. |
| 2006/0135972 A1 | * | 6/2006 | Zeiner ........................ 606/167 |
| 2006/0167406 A1 | * | 7/2006 | Quinn ...................... 604/96.01 |
| 2007/0078397 A1 | * | 4/2007 | Weststrate ............. 604/164.01 |
| 2007/0233005 A1 | * | 10/2007 | McMichael et al. .... 604/164.01 |

FOREIGN PATENT DOCUMENTS

| | | |
|---|---|---|
| JP | 8-506249 | 7/1996 |
| WO | 2005/112801 A2 | 12/2005 |

OTHER PUBLICATIONS espacenet English abstract of JP 8-50649.
Inoue, Nobuyuki, et al., "A new PEG technique 'Direct Method' and fistula infection", *Department of Internal Medicine, Department of Pathology, Suita Municipal Hospital*, Osaka, vol. 9, No. 1 2005, pp. 79-83, translation, pp. 1-3.

* cited by examiner

*Primary Examiner*—Nicholas D Lucchesi
*Assistant Examiner*—Victoria P Campbell
(74) *Attorney, Agent, or Firm*—Ladas and Parry LLP (57) ABSTRACT

A gastrostomy catheter introducing device includes a puncturing device 1 including a body 6 having a tube 4 and a flange 5, and a puncturing needle 7 axially slidably held in the tube 4 of the body 6; and a gastric wall fixating and fistula expanding device 2 including an outer tube 9 to be inserted into the tube 4 of the puncturing device 1, a gastrostomy catheter guide member 10 held inside the outer tube 9, a clip 11 swingably attached to an inner end part of the gastrostomy catheter guide member 10, and a clip turning member 12 having one end connected to the clip 11 to turn the clip 11.

4 Claims, 7 Drawing Sheets

GASTROSTOMY CATHETER INTRODUCING DEVICE

BACKGROUND OF THE INVENTION

1. Field of the Invention

The present invention relates to a gastrostomy catheter introducing device for percutaneous endoscopic gastrostomy.

2. Description of the Related Art

A patient incapable of oral injection is nourished by artificially feeding the patient through a nourishing tube inserted through the nose into the stomach. The nourishing tube extending outside from the nose spoils the appearance of the patient and gives a strong feeling of wrongness to the patient.

A nourishing method is employed to avoid spoiling the appearance of the patient and giving a feeling of wrongness to the patient. This nourishing method establishes a gastric fistula in the stomach by gastrostomy and supplies a nourishing liquid into the stomach through a catheter for gastrostomy (hereinafter referred to as "gastrostomy catheter) into the stomach.

Endoscopic gastrostomy methods are classified roughly into pull/push methods and introducer methods. The pull/push method catches a wire percutaneously inserted into the stomach with a snare or the like under endoscopic observation, pulls the guide wire outside through the mouth, connects a gastrostomy catheter to the guide wire, and pulls the gastrostomy catheter together with the guide wire into the stomach. A pull method pulls a gastrostomy catheter connected to the guide wire outside the stomach. A push method pushes a gastrostomy catheter put on the guide wire into the stomach.

The introducer method percutaneously thrusts a trocar having an inner needle and a sheath into the stomach, extracts the inner needle from the sheath, inserts a balloon gastrostomy catheter provided with a balloon through the sheath into the stomach, and inflates the balloon to fixate the balloon gastrostomy catheter.

The pull/push method is an easy method of establishing a gastric fistula. However, the pull/push method needs to pass the gastrostomy catheter through the oral cavity and the pharynx. Therefore, the pull/push method causes inflammation around the gastric fistula after gastrostomy unless the pull/push method is carried out by a clean operation.

The introducer method inserts the gastrostomy catheter into the stomach from outside the body and hence can be achieved by a clean operation. Therefore, it is expected that inflammation around the gastric fistula can be prevented after gastrostomy. However, the introducer method can use only the thin balloon gastrostomy catheter, the gastric fistula needs to be expanded at an early stage and the balloon gastrostomy catheter needs to be changed frequently. Thus the introducer method requires troublesome management after the operation.

An improved introducer method developed through the improvement of the introduction method is proposed in "Atarashii Irou Zousetsu-hou (direct method) to Irou Kansen (New Gastrostomy and Fistula Infection)", Zaitaku Iryou to Naishikyou Chiryou, pp. 79-89, July, 2005. This improved introducer method detains a thick bumper type gastrostomy catheter, such as a button type gastrostomy catheter used by the pull/push method, in the stomach.

The improved introducer method fixates three or four parts of the stomach to the abdominal wall with threads or T-fasteners to restrain the stomach from moving relative to the abdominal wall before thrusting a trocar into the stomach. Then, the improved introducer method thrusts a thin trocar through a central part of the fixed part of the stomach into the stomach, detains a guide wire on the stomach, incises the skin to form an opening, bluntly expands the opening to introduce air sufficiently into the stomach, and then pushes a gastrostomy catheter into the stomach.

The improved introducer method needs to supply a sufficient amount of air into the stomach to fixate the stomach to the abdominal wall and to secure a sufficient field of view which can be viewed through an endoscope. Moreover, since air pressure in the stomach is only means for holding the front wall of the stomach against pressure applied to the front wall of the stomach when the gastrostomy catheter is thrust into the stomach, the front wall of the stomach is moved near to the rear wall of the stomach and a field view which can be viewed through an endoscope cannot be secured in some cases when the gastrostomy catheter is thrust into the stomach. It is possible that excessive air supply into the stomach causes the leakage of air into the abdominal cavity (tympanites) and gastrostomy cannot be achieved.

The improved introducer method needs an additional gastric wall fixing implements for gastric wall fixation essential to the improved introducer method and may possibly puncture other adjacent organs, such as the liver and the transverse colon, because the improved introducer method needs to puncture several parts of the stomach and the abdominal wall. If the parts of the gastric wall fixed to the abdominal wall are excessively spaced apart, the gastric wall will excessively slacken and, in some cases, the gastrostomy catheter cannot be successfully inserted into the stomach. If the parts of the gastric wall fixed to the abdominal wall are excessively close to each other, the gastric wall cannot be expanded and, in some cases, the gastrostomy catheter cannot be successfully inserted into the stomach.

SUMMARY OF THE INVENTION

The present invention has been made to solve the foregoing problems and it is therefore an object of the present invention to provide a gastrostomy catheter introducing device capable of making it possible to achieve both the fixation of the stomach to the abdominal wall and the expansion of a part through which a gastrostomy catheter is inserted into the stomach by a single cycle of a puncturing operation and of preventing the leakage of air from the stomach during operations.

A gastrostomy catheter introducing device according to the present invention includes: a puncturing device, for forming fistulas through the abdominal wall and the gastric wall, including a body including a tube, a flange formed on an outer end part of the tube, and a puncturing needle axially slidably held in the tube of the body; and a gastric wall fixating and fistula expanding device, for fixating the stomach to the abdominal wall and expanding fistulas, including an outer tube to be inserted into the tube of the puncturing device, a gastrostomy catheter guide member held inside the outer tube, a clip attached to an inner end part of the gastrostomy catheter guide member so as to be swingable, and an operating member having one end connected to the clip to turn the clip.

According to the present invention, fixation of the stomach to the abdominal wall and expansion of a gastric fistula through which the gastrostomy catheter is inserted into the stomach can be simultaneously accomplished by a single cycle of a puncturing operation, the movement of the front gastric wall toward the rear gastric wall can be prevented by pulling a part around the gastric fistula of the front gastric wall to secure a proper field of view which can be viewed through an endoscope, and damaging the rear gastric wall by the gastrostomy catheter inserted into the stomach can be avoided by inserting the gastrostomy catheter into the stomach along the gastrostomy catheter guide member of the gastric wall fixating and fistula expanding device.

According to the present invention, the tube of the puncturing device may be provided with a continuous slit extending between the opposite ends thereof to facilitate the insertion of the gastric wall fixating and fistula expanding device into the tube of the puncturing device.

According to the present invention, the gastrostomy catheter guide member of the gastric wall fixating and fistula expanding device may be formed in a shape substantially resembling a long shoehorn such that a bumper type gastrostomy catheter can be correctly inserted into the stomach observing the interior of the stomach through an endoscope.

According to the present invention, the open end of the outer end part of the outer tube of the gastric wall fixating and fistula expanding device may be covered with a bag to prevent the leakage of air from the stomach during operations.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
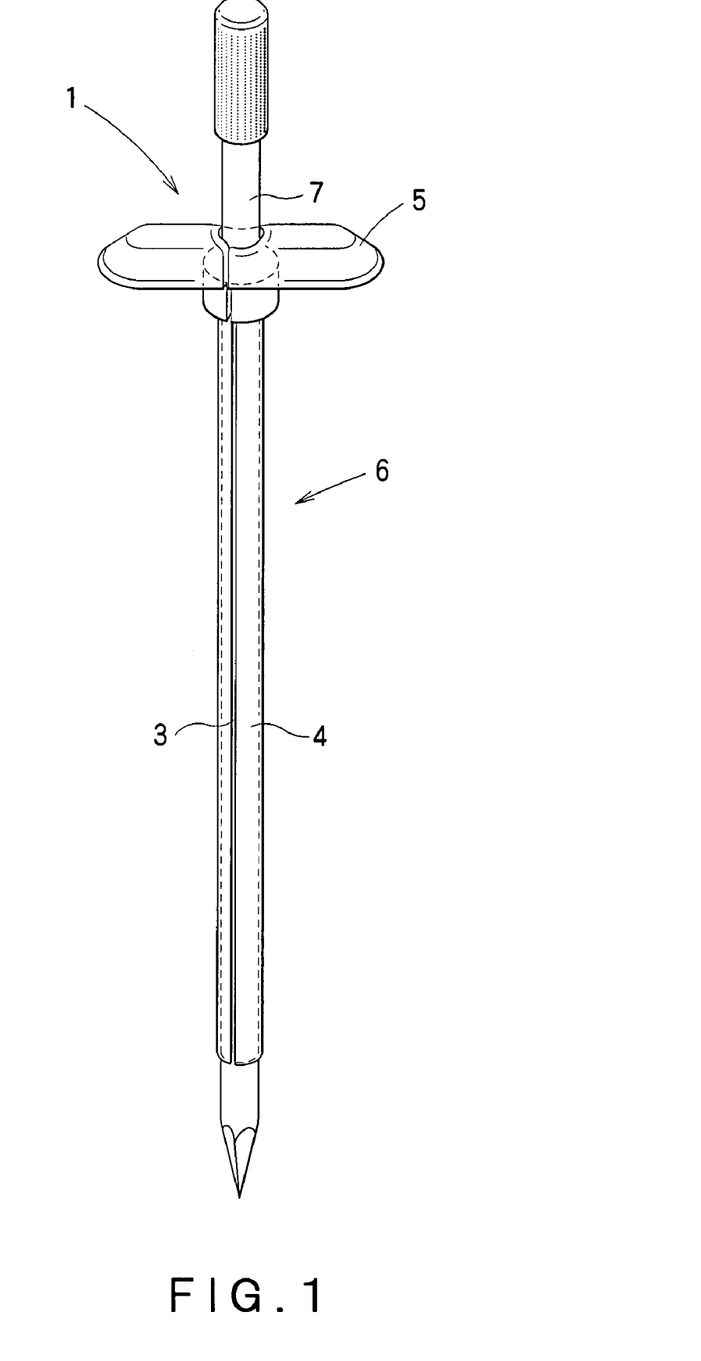
FIG. 1 is a perspective view of a puncturing device included in a gastrostomy catheter introducing device in a preferred embodiment according to the present invention.
Figure 2:
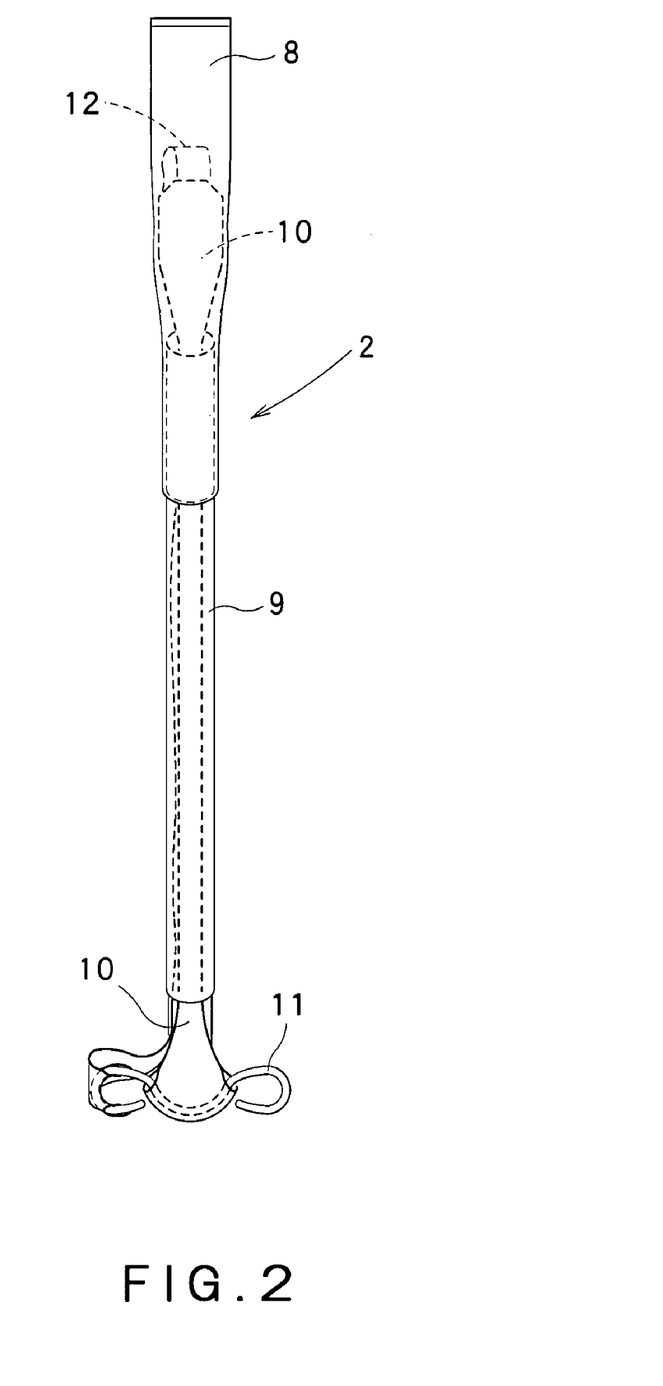
FIG. 2 is a perspective view of a gastric wall fixating and fistula expanding device included in the gastrostomy catheter introducing device embodying the present invention.

Referring to FIGS. 1 and 2, a gastrostomy catheter introducing device in a preferred embodiment according to the present invention includes a puncturing device 1 for forming fistulas in the patient's abdominal wall (hereinafter, referred to simply as "the abdominal wall") and the patient's gastric wall (hereinafter referred to simply as "the gastric wall"), and a gastric wall fixating and fistula expanding device for fixating the patient's stomach (hereinafter referred t simply as "the stomach") to the abdominal wall and expanding the fistulas formed in the abdominal wall and the gastric wall.

Referring to FIG. 1, the puncturing device 1 includes a body 6 including a tube 4 provided with a longitudinal slit 3 and a flange 5 on an outer end part of the tube 4; and a puncturing needle axially slidably inserted in the tube 4 of the body 6.

Preferably, the tube 4 of the body 6 is a round tube made of a hard plastic material and having a length between 6 and 10 cm and an inside diameter of 6 mm. The tube 4 may be made of a soft plastic material. The puncturing needle 7 is, for example, a 16 F trocar. The puncturing needle 7 can slide in the tube 4 and can be percutaneously thrust into the stomach. The puncturing needle 7 forms fistulas in the abdominal wall 22 and the gastric wall 21.

Figure 3:
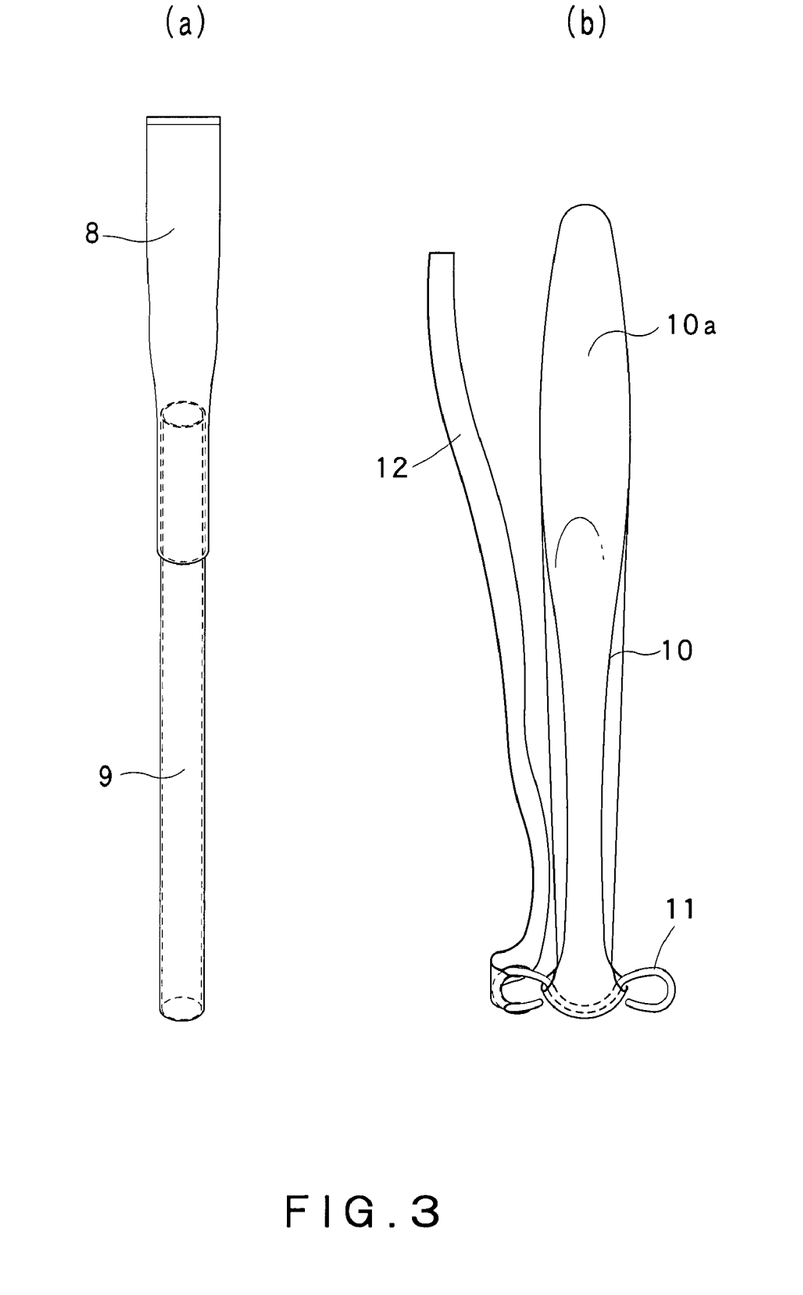
FIG. 3 is an exploded perspective view of the gastric wall fixating and fistula expanding device shown in FIG. 2.

Referring to FIGS. 2 and 3, the gastric wall fixating and fistula expanding device 2 includes an outer tube 9, a bag 8 of a thin plastic film attached to an outer end part of the outer tube 9 so as to close the open end of the outer end part of the outer tube 9, a gastrostomy catheter guide member 10 held inside the outer tube 9, a clip 11 swingably attached to an inner end part of the gastrostomy catheter guide member 10, a clip operating member 12 having one end connected to the clip 11 and extended through the gastrostomy catheter guide member 10. The outer tube 9 has an outside diameter of 6 mm and a length between 12 and 17 cm. The outer tube 9 is inserted in the tube 4 after the puncturing needle 7 of the puncturing device 1 has been extracted from the tube 4.

The gastrostomy catheter guide member 10 is formed by molding a hard plastic material in a shape substantially resembling a long shoehorn and has a sectional shape resembling a circular arc. Preferably, the gastrostomy catheter guide member 10 has an overall length of 20 cm. The gastrostomy catheter guide member 10 has an inner end part of a width of 15 mm and an outer end part of a width of 10 mm. The gastrostomy catheter guide member 10 has a continuous guide surface 10a extending between the opposite ends thereof. A bumper part of a bumper type gastrostomy catheter, not shown, slides along the concavely circular guide surface 10a of the gastrostomy catheter guide member 10.

The clip 11 is made of a hard plastic material and has a length of 26 mm and a width of 5 mm. The clip 11 is held inside the outer tube 9 with the length thereof extended longitudinally in the outer tube 9. When the clip 11 is pushed entirely out of the outer tube 9, the clip 11 extends perpendicularly to the length of the gastrostomy catheter guide member 10 in engagement with a part around the gastric fistula of the gastric wall.

The operating member 12 is a laminated tape formed by laminating soft plastic films. The operating member 12 has an inner end connected to one of the opposite ends of the clip 11 swingably attached to the inner end part of the gastrostomy catheter guide member 10.

The operating member 12 is pulled to turn the clip 11 so that the clip 11 may extend along the gastrostomy catheter guide member 10 after the gastrostomy catheter has been introduced into the stomach along the gastrostomy catheter guide member 10 to remove the gastrostomy catheter guide member 10.

The operation of the gastrostomy catheter introducing device of the present invention will be described. First, an endoscope 20 is inserted into the gastric cavity 21a of the stomach 21, and the gastric juice remaining in the stomach 21 is sucked out to facilitate observing the interior of the stomach 21. Subsequently, air is supplied through the endoscope 20 into the gastric cavity 21a of the stomach 21 to inflate the stomach 21 sufficiently. Then, the inside surface of the gastric cavity 21a of the stomach 21 is observed through the endoscope 20 using an optical sign or a digital sign to determine a part to be punctured. The skin of the abdomen is anesthetized by local anesthesia, and an incision of about 15 mm in length is formed in the abdominal wall 22.

Figure 4A:
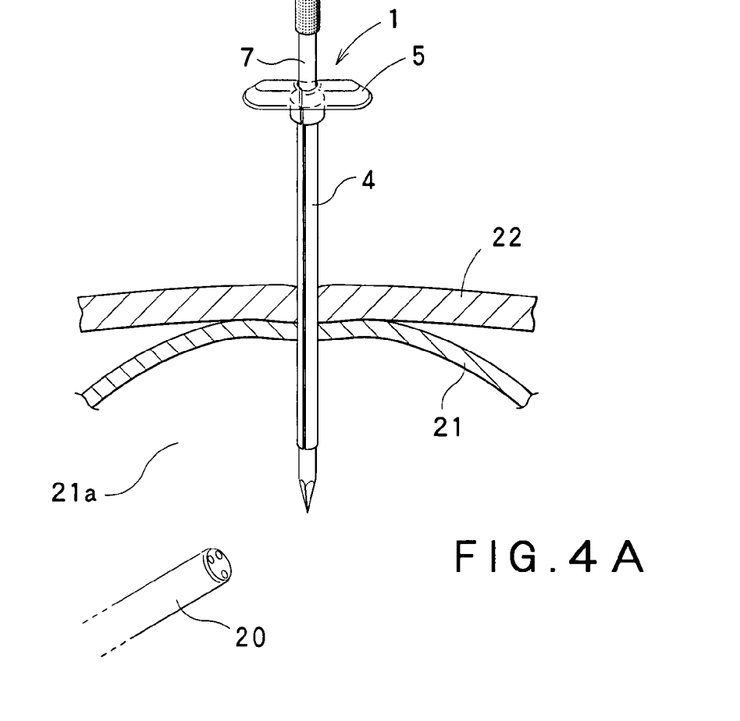
FIG. 4A is a view of assistance in explaining the operation of the puncturing device shown in FIG. 1.
Figure 4B:
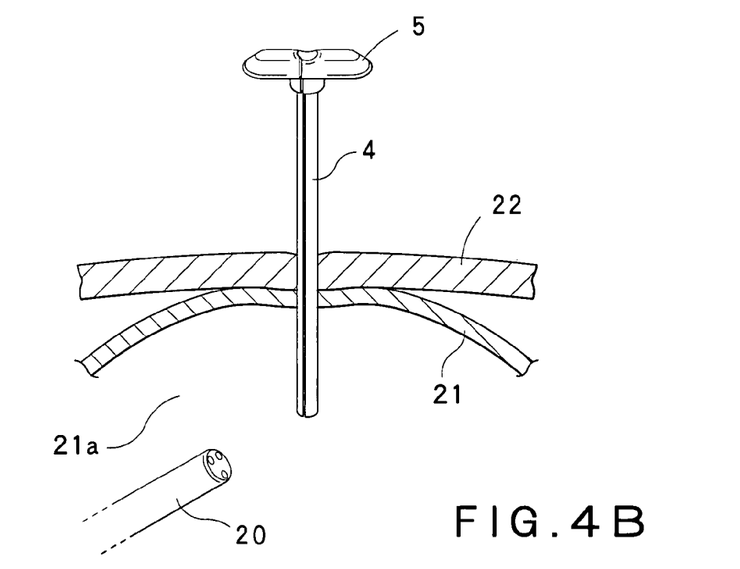
FIG. 4B is a view of assistance in explaining the operation of the puncturing device shown in FIG. 1.

Then, the incision in the abdominal wall 22 is expanded with a pair of Péan forceps, not shown, to form an opening in the abdominal wall 22. Then, the puncturing needle 7 of the puncturing device 1 is percutaneously thrust into the gastric cavity 21a of the stomach as shown in FIG. 4A. After the confirmation of the penetration of the outer tube 4 of the puncturing device 1 into the gastric cavity 21a of the stomach 21 by observation through the endoscope 20, the puncturing needle 7 is extracted from the outer tube 4 as shown in FIG. 4B. A finger is put on the open outer end of the outer tube 4 after the puncturing needle 7 has been extracted from the outer tube 4 to prevent air contained in the stomach 21 from leaking through the outer tube 4.

Figure 5A:
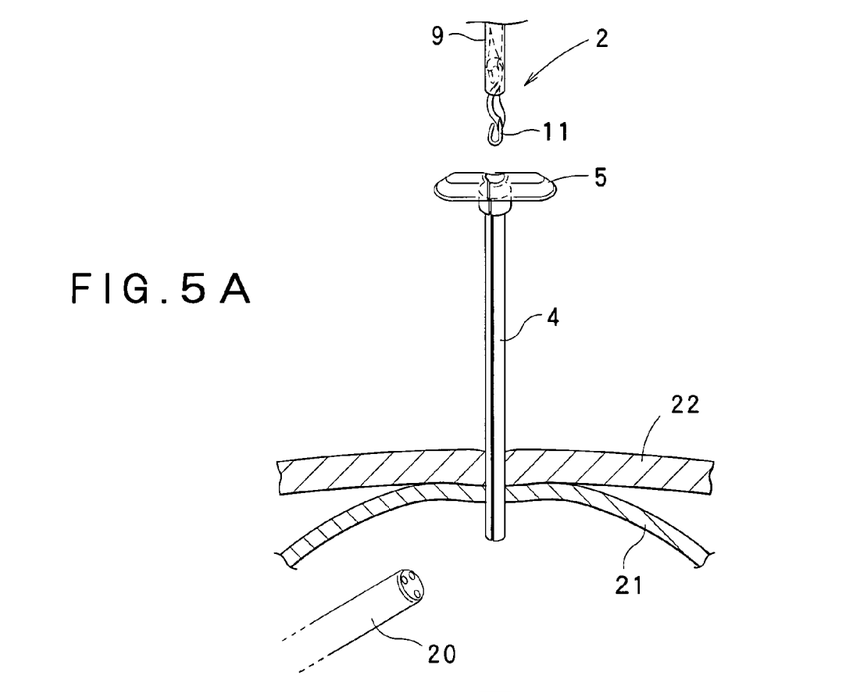
FIG. 5A is a view of assistance in explaining the step of inserting the gastric wall fixating and fistula expanding device into the puncturing device.
Figure 5B:
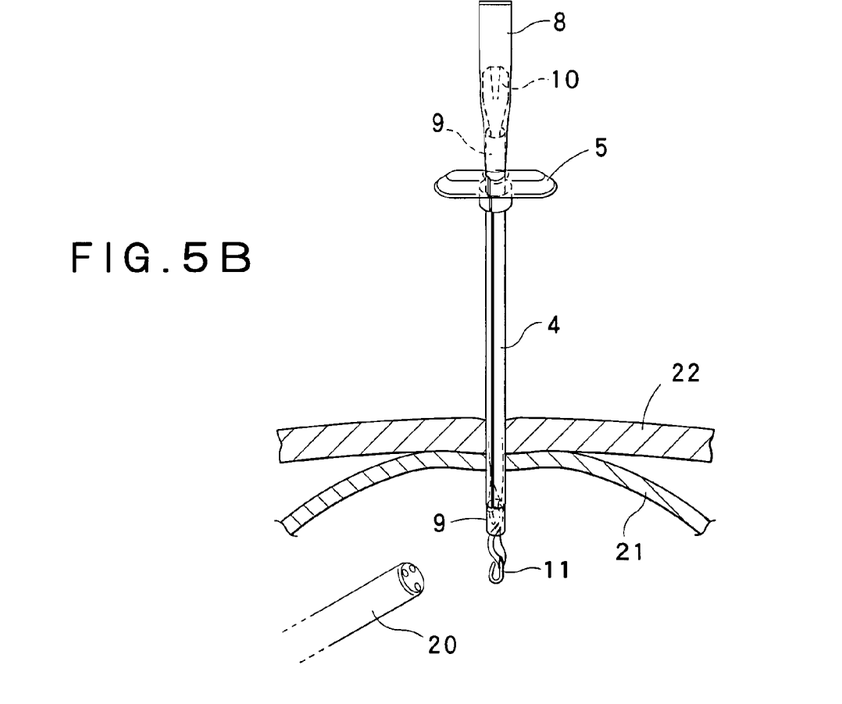
FIG. 5B is a view of assistance in explaining the step of inserting the gastric wall fixating and fistula expanding device into the puncturing device.

Then, the gastric wall fixating and fistula expanding device 2 is held right above the outer tube 4 of the puncturing device 1 as shown in FIG. 5A. Then, the gastric wall fixating and fistula expanding device 2 is lowered and the outer tube 9 of the gastric wall fixating and fistula expanding device 2 is pushed into the outer tube 4 of the puncturing device 1 as shown in FIG. 5B.

At this stage of gastrostomy, the clip 11 of the gastric wall fixating and fistula expanding device 2 is partly projected from the inner end of the outer tube 9 and extends along the length of the outer tube 9. Since the open outer end of the outer tube 9 is covered in an airtight fashion with the bag 8, air contained in the gastric cavity 21a of the stomach 21 is unable to leak through the outer tube 9.

Figure 6A:
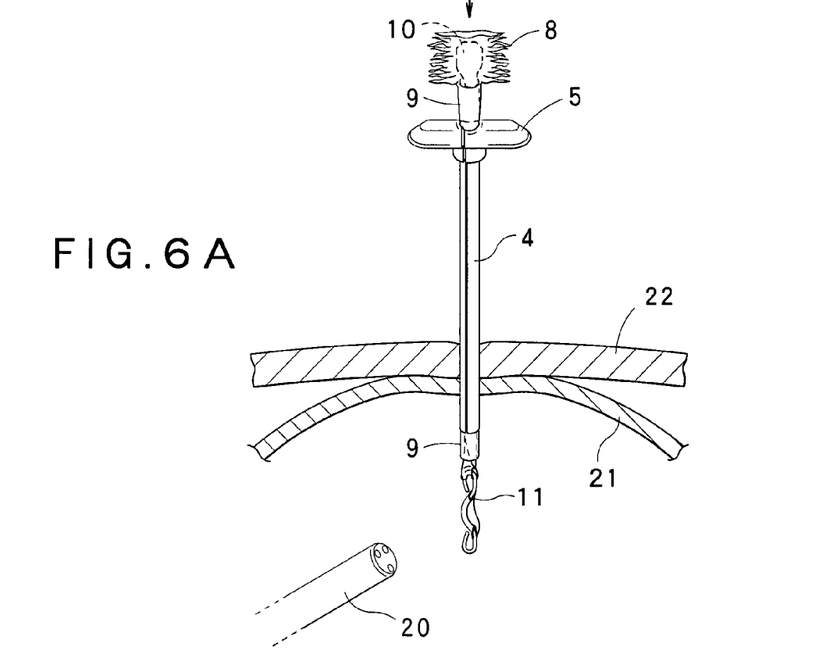
FIG. 6A is a view of assistance in explaining the operation of the gastric wall fixating and fistula expanding device.

Then, the gastrostomy catheter guide member 10 of the gastric wall fixating and fistula expanding device 2 is pushed down further through the soft bag 8. The gastrostomy catheter guide member 10 slides along the outer tube 9 into the stomach 21. Consequently, the clip 11 attached to the inner end part of the gastrostomy catheter guide member 10 projects completely from the outer tube 9 as shown in FIG. 6A.

Figure 6B:
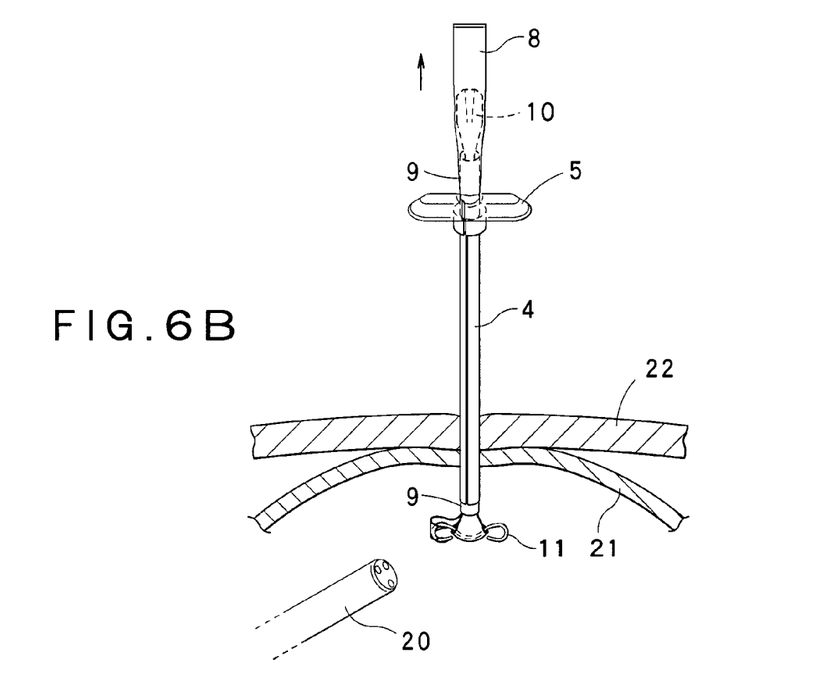
FIG. 6B is a view of assistance in explaining the operation of the gastric wall fixating and fistula expanding device.

After the confirmation of the complete projection of the clip 11 attached to the inner end part of the gastrostomy catheter guide member 10 from the outer tube 9 by observation through the endoscope 20, an outer end part of the gastrostomy catheter guide member 10 is gripped through the soft bag 8 and the gastrostomy catheter guide member 10 is pulled outward. Consequently, the clip 11 attached to the inner end, part of the gastrostomy catheter guide member 10 is turned and extends perpendicularly to the gastrostomy catheter guide member 10 as shown in FIG. 6B. Thus the gastric wall fixating and fistula expanding device 2 is unfolded in a T-shape with the gastrostomy catheter guide member 10 vertically extended and the clip 11 horizontally extended.

Subsequently, the outer tube 4 of the puncturing device 1 and the gastric wall fixating and fistula expanding device 2 are held by hand and are pulled out of the body. Since the clip 11 attached to the inner end part of the gastrostomy catheter guide member 10 is stopped by a part around the punctured part of the gastric wall 21, the gastrostomy catheter guide member 10 cannot be removed from the body and is held at the punctured part of the gastric wall 21.

Figure 7:
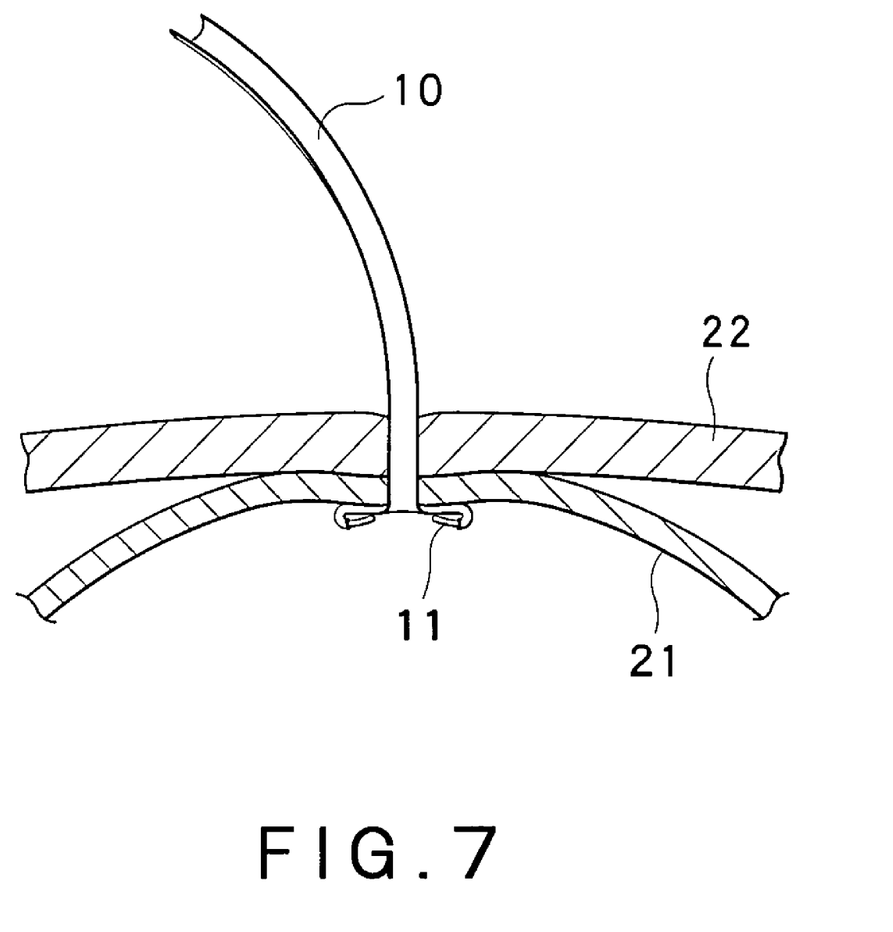
FIG. 7 is a view of a gastrostomy catheter guide member attached to the gastric wall fixating and fistula expanding device.

The outer end part of the gastrostomy catheter guide member 10 is grasped by the left hand and is pulled up to fixate the gastric wall 21a of the stomach 21 on the abdominal wall 22 with the clip 11 as shown in FIG. 7. Thus the gastric wall 21a is naturally expanded.

A bumper type gastrostomy catheter is inserted into the stomach 21 by a method similar to a percutaneous bumper type gastrostomy catheter changing method. The gastrostomy catheter guide member 10 is grasped. An obturator is attached to the bumper of the bumper type gastrostomy catheter, an inner end part of the bumper type gastrostomy catheter is stretched, and the bumper type gastrostomy catheter is inserted along the gastrostomy catheter guide member 10 into the stomach 21.

After the confirmation of the entrance of the bumper of the bumper type gastrostomy catheter into the stomach 21 by observation through the endoscope 20, the gastrostomy catheter guide member 10 is pushed down toward the stomach 21, and then the clip 11 attached to the inner end part of the gastrostomy catheter guide member 10 is turned so as to extend along the gastrostomy catheter guide member 10 by pulling the operating member 12 connected to the clip 11 to disengage the clip 11 from the part around the gastric fistula of the gastric wall 21a. Then, the operating member 12 is pulled further to pull the gastrostomy catheter guide member 10 together with the clip 11 out of the body. Thus gastrostomy is accomplished.

According to the present invention, fixation of the stomach to the abdominal wall and expansion of the gastric fistula can be simultaneously accomplished by a single cycle of a puncturing operation, the bumper of the bumper type gastrostomy catheter is guided by the gastrostomy catheter guide member when the bumper type gastrostomy catheter is passed through the gastric fistula. Thus the bumper of the bumper type gastrostomy catheter can be surely inserted into the stomach.

Although the invention has been described in its preferred embodiment with a certain degree of particularity, obviously many changes and variations are possible therein. It is therefore to be understood that the present invention may be practiced otherwise than as specifically described herein without departing from the scope and spirit thereof.

What is claimed is:

1. A gastrostomy catheter introducing device comprising:
   a puncturing device including:
      a body having a tube and a flange, and
      a puncturing needle axially slidably held in the tube of the body; and
   a gastric wall fixating and fistula expanding device including:
      an outer tube to be inserted into the tube of the puncturing device,
      a gastrostomy catheter guide member held inside the outer tube,
      a clip swingably attached to an inner end part of the gastrostomy catheter guide member so as to extend parallel to the outer tube holding the gastrostomy catheter guide member therein, and
      a clip turning member having one end connected to the clip and extended through the gastrostomy catheter guide member to turn the clip such that the clip extends perpendicularly to the outer tube.

2. The gastrostomy catheter introducing device according to claim 1, wherein the tube of the puncturing device is provided with a longitudinal slit extending between opposite ends thereof.

3. The gastrostomy catheter introducing device according to claim 1, wherein the gastrostomy catheter guide member has a shape substantially resembling a long shoehorn.

4. The gastrostomy catheter introducing device according to claim 1, wherein a bag is attached to an outer end part of the outer tube of the gastric wall fixating and fistula expanding device so as to cover an open end of the outer end part of the outer tube.

* * * * *